(12) United States Patent
Johnson

(10) Patent No.: US 7,371,069 B2
(45) Date of Patent: May 13, 2008

(54) MANIKIN AND EYE DEVICE APPARATUS, METHODS AND ARTICLES OF MANUFACTURE

(75) Inventor: Brian Johnson, Hayward, WI (US)

(73) Assignee: Tohickon Johnson Development LLC, Wilmington, DE (US)

( * ) Notice: Subject to any disclaimer, the term of this patent is extended or adjusted under 35 U.S.C. 154(b) by 653 days.

(21) Appl. No.: 10/797,232

(22) Filed: Mar. 10, 2004

(65) Prior Publication Data

US 2004/0198164 A1    Oct. 7, 2004

(51) Int. Cl.
*G09B 23/00* (2006.01)

(52) U.S. Cl. ..................................... 434/295

(58) Field of Classification Search ............... 434/262, 434/267, 270, 271, 295, 296; 446/301, 341, 446/389, 392; 264/46.4
See application file for complete search history.

(56) References Cited

U.S. PATENT DOCUMENTS

| | | |
|---|---|---|
| 2,820,325 A | 1/1958 | Prupis |
| 4,432,919 A | 2/1984 | Rinehart |
| 4,477,500 A * | 10/1984 | Powell ..................... 428/16 |
| 4,511,522 A | 4/1985 | Rinehart |
| 4,515,340 A | 5/1985 | Rinehart |
| 4,596,683 A | 6/1986 | Powell |
| 4,637,159 A | 1/1987 | Kulis |
| 4,642,209 A | 2/1987 | Powell |
| 4,705,488 A | 11/1987 | Bohl, Jr. et al. |
| 4,753,412 A * | 6/1988 | Johnson .................... 249/55 |
| 5,087,204 A * | 2/1992 | Thompson ................ 434/296 |
| 5,645,780 A * | 7/1997 | Rinehart .................. 264/46.4 |
| 5,735,895 A * | 4/1998 | Rinehart .................. 623/6.56 |
| 6,007,881 A * | 12/1999 | Lennard .................... 428/16 |
| 6,500,045 B1 * | 12/2002 | Secrist .................... 446/389 |
| 6,811,461 B2 * | 11/2004 | Maddocks et al. ......... 446/392 |

* cited by examiner

*Primary Examiner*—Kurt Fernstrom
(74) *Attorney, Agent, or Firm*—Dilworth Paxson LLP

(57) ABSTRACT

Apparatus, methods and articles of manufacture are disclosed for installing an artificial eye in a realistic, life-like sculpture, comprising an artificial eye of partially hemispherical shape, as well as a manikin with an eye-mounting area adapted to mate with such an artificial eye without risk of subsequent movement of the eye or of distortion of the features surrounding the eye-mounting area of the sculpture. Eye mounting pieces for retrofitting existing sculptures having conventional eye mounting areas to permit the accurate and life-like mounting of artificial eyes are also provided.

17 Claims, 3 Drawing Sheets

MANIKIN AND EYE DEVICE APPARATUS, METHODS AND ARTICLES OF MANUFACTURE

CROSS REFERENCE TO RELATED APPLICATIONS

This application claims priority to U.S. Provisional Patent Application No. 60/331,316, filed Nov. 14, 2001, and U.S. patent application Ser. No. 10/247,063, filed on Sep. 18, 2002, now U.S. Pat. No. 6,923,654, each of which is incorporated herein in its entirety.

FIELD OF THE INVENTION

The present invention relates generally to apparatus, methods and articles of manufacture for sculptured bodies and artificial eyes therefor. More particularly, this invention relates to apparatus, methods and articles of manufacture for making manikins and realistically installing artificial eyes therein.

BACKGROUND OF THE INVENTION

The construction of life-like and realistic sculptures, e.g., taxidermy mounts (built upon underlying "manikin" sculptures), clothing mannequins, dolls, artistic sculptures, etc., can be extremely difficult. Every body part must be accurately depicted for the sculpture to be acceptable. Yet accurately depicting body parts, and assembling them into a pleasing whole, often requires the expert mastery of skills, such as sculpting, painting, etc.

One area that is especially difficult is eye construction and placement. This is because, albeit artificial, the eyes must be realistic for the sculpture to appear life-like. Realistic artificial eye construction and placement involve a number of factors, including: the shape of the eye; materials to be used for the eye; alignment and location of the eye on the face of the sculpture; and mounting and placement of the eye in the sculpture. Each of the foregoing factors, as further described below, adds complications to the sculpting process.

The shape of the eye is usually generally hemispherical, or approximately half of a circle. This shape has provided prior art sculptures with mounting points for clay, epoxy, etc. (see, e.g., U.S. Pat. Nos. 4,432,919, 4,511,522, 4,515,340, 5,645,780 and 5,735,895 to Rinehart; U.S. Pat. Nos. 4,642,209, 4,596,683 and 4,477,500 to Powell; and U.S. Pat. No. 6,00,881 to Lennard). However, due to mounting difficulties, hemispherical eyes do not necessarily provide a life-like installed eye on a taxidermy manikin.

Materials used to make artificial eyes vary. Usually in taxidermy, glass eyes are used, as they provide a good resemblance to natural eyes. Other transparent materials, such as acrylics, may be used as well. Nevertheless, the material must be chosen carefully, as it may fade or crack, thereby ruining the sculpture.

The alignment and location of the eye is critical to the finished sculpture, and must be accurate to produce a life-like result. A sculpture in the taxidermy arts, for instance, usually begins with an animal and a properly sized manikin (usually made of foam and often mass produced), which is prepared by adding appropriate external features, such as ears, eyes, antlers (if present), and the like. For antlers, usually the natural antlers are used, but the remaining external organs are artificial.

For an animal mount, the original animal is skinned and the skin is tanned. Then the skin is placed over the selected manikin and the finishing work done. The manikin provides the infrastructure for the skin or "cape," yet the size and placement of the artificial eyes, ears, and the like, must correspond with the external organs of the original animal. Thus, customization work by the taxidermist is required to ensure that mass produced foam manikins and the artificial organs match the unique natural infrastructure and features of the animal being mounted in size and shape.

To assist in the placement of artificial eyes on the customized manikins, the manikin design may have "preset" or other designations of eye location. If the manikin does not have designated eye locations, the taxidermist must place the eyes in an appropriate area on the face, which can be very problematic. Then eyelids and other eye-surround contour features are added by the taxidermist, typically using clay or foam. When clay is used, the animal skin is usually lifted onto the manikin, and the eyelid skin is typically pushed onto the clay and adjusted so as to create a life-like appearance of the eyes.

It requires significant artistic skill, time, anatomical knowledge, and experience to recreate eyes and eyelids in a taxidermy manikin so that they look natural and symmetrical. If the pupil is not centered within the eye socket, for example, the eye may be misplaced. Also, if the eye is not located so that it appears to be looking in a life-like direction on the mounted animal, the entire completed mount will appear unnatural. Moreover, for example, some animal species characteristically look downward as well as forward, and so the appropriate downward angle must be established.

The problems are exacerbated because, of course, eyes are paired in nature, so most realistic sculptures have two eyes. Thus, the eye placement problems are magnified because alignment and retention complications need to be considered for both of the eyes. In other words, each of the two eyes must be properly aligned, each with the other, as well as in relation to the overall animal to create a life-like appearance. In a conventional mount, matching the focus of the two eyes can require hours, and require significant sculpting ability.

Artificial eyes may be set and fixed in, for example, a taxidermy mount, in a number of ways, such as by using epoxy, clay, and the like. However, often such materials have their drawbacks. For instance, epoxy may harden to the extent that it causes the eye to crack. Eye mounting clay is very soft and tends to move when the skin is attached to the manikin, thus distorting the eyelids or making it very difficult to pin the skin in place around the eye. When the skin and clay dry, they shrink; often to the extent that the eyelids move and lose shape and/or symmetry. Additionally, the softer clay takes a considerable amount of time to dry, and as a result the entire sculpture must be set aside, thereby delaying production while waiting for the clay to dry. Thus retaining the mounted eye in the initially desired position (e.g., forward and downward as noted above) may be very difficult.

Attempts have been made to resolve these complications relating to setting the artificial eyes and the surrounding eyelids in the taxidermy mount. For example, a taxidermy manikin may contain a pre-formed eye socket. A system of setting eyes into a mold and pouring foam around the eye to form a foam eyelid is described in U.S. Pat. No. 4,753,412 (the "preset" technique). However, by this method eyes are not consistently insert-molded into the manikin without the possibility of rotation to an incorrect orientation or displacement. The preset eye may not be at the proper angle for a particular specimen, or may not appropriately convey a desired expression. Moreover, the eye may shift as the foam rises and squeezes between the eye and the mold, or the method may fail to maintain the desired eye placement during curing of the foam.

Another attempted solution has been to anchor an eye by use of notches, screws, and the like. Again, these devices often fail to provide proper placement for particular specimens, or they may not permit the taxidermist to appropriately convey a desired expression.

Thus, until the present invention, there has remained an unmet need in the art for simple apparatus and methods of artificial eye installation in realistic sculptures, such as taxidermy mounts, that will accurately and consistently produce an anatomically correct, life-like sculpture, or reliably achieve and maintain the desired artificial eye placement as determined without movement by the sculptor. In addition, it is desirable that such results be accomplished quickly, easily, inexpensively, and without a need for expert sculpturing skills.

SUMMARY OF THE INVENTION

The present invention provides apparatus, methods and articles of manufacture for accurately, consistently and efficiently installing artificial eyes or eyepiece inserts into taxidermy manikins or other life-like sculptures, such as dolls, toy animals, clothing mannequins, or other created bodies utilizing artificial eyes, thus overcoming difficulties inherent in conventional installation methods. In a preferred embodiment, a partially hemispherical eye is configured so as to permit mounting on either a manikin with eye recess or using an eye-mounting piece.

Advantageously, the present invention achieves desirable results using less glass to make modified partially hemispherical artificial eyes, thereby reducing costs. It is also quicker and easier, requiring less skill or time by the taxidermist to use the disclosed artificial eyes to create professional and realistic taxidermy mounts.

Other preferred embodiments also comprise a manikin with an eye socket that retains a partially hemispherical artificial eye in a mating configuration. Manikin embodiments also include an ability to be reconfigured so as to retain eyes in other shapes, e.g., conventional hemispherical eyes.

Additional embodiments comprise an eye mounting-piece configured so as to retain a partially hemispherical eye. These embodiments may be used to retrofit manikins that have other shapes of eye sockets (e.g., standard hemispherical eye sockets) or no eye sockets at all.

Methods are also disclosed of mounting a partially hemispherical eye, in a manikin with an eye socket, an eye-mounting piece, or in a reconfigured eye mount. When an eye mounting-piece is used, it may then be mounted on a manikin.

Apparatus are also disclosed, comprising in preferred embodiments a partially hemispherical artificial eye and manikin with mating eye socket. Yet other apparatus embodiments comprise a partially hemispherical eye and eye mounting piece, for retrofitting into an existing manikin.

Therefore, it is an object of the present invention to provide simple, accurate apparatus and methods of artificial eye installation in realistic and life-like sculptures.

It is a further object of the present invention to provide apparatus, methods and articles of manufacture for installing artificial eyes in realistic, like-like sculptures, including taxidermy manikins.

Additional objects, advantages and novel features of the invention will be set forth in part in the description and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

DETAILED DESCRIPTION OF PREFFERRED EMBODIMENTS

Reference is now made to the accompanying Figures for the purpose of describing, in detail, preferred embodiments of the present invention. Like elements have the same numbers throughout the several views, for example, with reference to artificial eyepiece 10, pupil 13, and eye mounting area 40 on the taxidermy manikin. The detailed description accompanying each Figure is not intended to limit the scope of the claims appended hereto.

Figure 1:
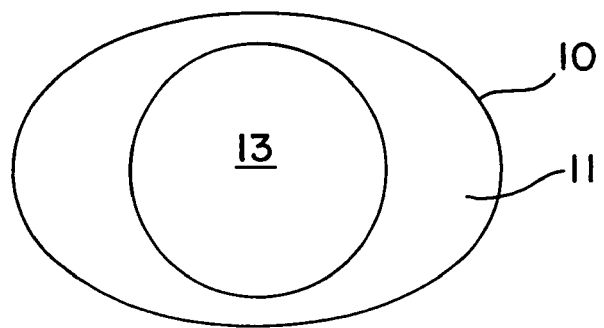
FIG. 1 shows a front view of a preferred artificial eye embodiment.

FIG. 1 depicts a preferred embodiment of an artificial eye 10. The curved front surface 11 of the eye is generally visible when installed on a manikin. The pupil 13, although present in this view, may or may not be present in any particular embodiment; that is, the user may prefer to add a pupil (and/or any other coloration) later in the process. As a result, in such an embodiment, the artificial eye would not have a pupil in its original preparation.

It should be noted that in the various embodiments of the present invention, the eye 10 is modeled according to the visible surface of a natural eye of the species depicted in the sculpture. Naturally occurring eyes generally have the shape of a partial hemispherical in which the outer curved surface is visible on the face. By "hemisphere" is meant half of a sphere cut into two equal parts on a lateral plane through the midpoint of the sphere, which in the conventional artificial eye is solid, having two surfaces—a curved front surface forming the visible outer surface of the artificial eye when in use in a manikin—and a flat surface having the approximate diameter of the sphere, on the plane of which the sphere was divided, and forming the back of the artificial eye used to mount the eye to the manikin.

As known in the art, however, visible eye surfaces of different species vary by shape and size. This is generally true, even for different sized animals of the same species. For example, in life, a deer has a differently shaped visible eye surface than a bear or a fish. Therefore, an artificial eye embodiment for a deer would be differently shaped than an embodiment for a bear or a fish. Each embodiment for the deer, bear or fish would, however, have a partially hemispherical shape. Indeed, no matter what natural model is used for the artificial eye, any eye embodiment of the present invention has a curved hemispherical or partially hemispherical front surface. Essentially all of the hemispherical curved surface is visible in the bulging eye of a fish, but more often, in most animals, the visible surface is considered partially hemispherical.

In this disclosure when part of the otherwise curved hemispheric surface of the eye is covered by an upper or lower eyelid or eye socket, the full curve of the hemisphere is not completely visible, although it may still lie under the lid, and the visible surface is considered to be "partially hemispherical." The resulting general appearance of a partial hemispherical eye is essentially a slice of a sphere comprising an angle θ that is less than 180° of the arc of the sphere. The slice could represent less than 150° of the arc of the sphere, or less than 120° of the arc of the sphere, or even 90° or less of the arc of the sphere. If the eye is intended to represent a partially closed or squinted eye in the taxidermy mount the visible partially hemispheric curved surface of the artificial eye could represent only 45° to 90° of the arc of the sphere, or even less than 45°.

The exact included angle on any given eye embodiment depends upon the species for which that eye is molded. For example, Species X may have a partially hemispherical shape with an included angle of 45°, whereas Species Y may have a partially included angle of 95°.

Moreover, it should be noted, however, that use of the term "partially hemispherical" herein is meant to include an uneven surface, or elliptical variants and the like of the mounted artificial eye. That is, the curved, visible, front surface of a naturally occurring eye may not have a perfectly spherical curve, although it would still generally have a partially hemispherical surface. For example, a natural eye typically is aspheric: it bulges slightly in the area of the pupil. An eye embodiment according to the present invention might do so as well. As another example, a natural eye might resemble more of an elliptical cross section in its appearance, rather than a circular cross section typically found in the cross-sectional plane of a sphere. Accordingly, the term "partially hemispherical" as used herein is meant to include such naturally occurring or desired variants, as well. One of ordinary skill would understand the naturally occurring geometric variant shapes of the eye that, nevertheless, would be generically considered to be partially hemispherical in shape.

Moreover, the preferred artificial eye embodiments are not, and need not be, exact copies of natural eyes. They typically have a slightly greater surface area, albeit still within an included angle θ of less that 180°, as compared with the visible surface area of an eye in a living animal. This provides room for mounting, specifically room for tucking the cape around the eye, without unnaturally diminishing the visible surface area of the eye in the completed mount. Of course, insofar as eye size is dependant to a degree on the specimen size—e.g., in nature a 250 pound whitetail deer will usually have larger eyes than a comparable 150 pound whitetail deer—surface area determination of an artificial eye in a taxidermy mount of the animal is variable according to the size of the selected specimen. In the alternative, embodiments may be used that have little or no extra surface area for a larger specimen, but have extra surface area for a smaller specimen.

Additionally, although the preferred embodiments have a slightly greater surface area than a natural eye, embodiments may be used that have the same or even a smaller visible surface area as compared with a natural eye for a number of reasons, for example, mounting techniques, personal preferences, e.g., the mounted animal may be shown as if squinting into the sun, or in a resting pose with eyes partially closed, or the like.

Figure 2:
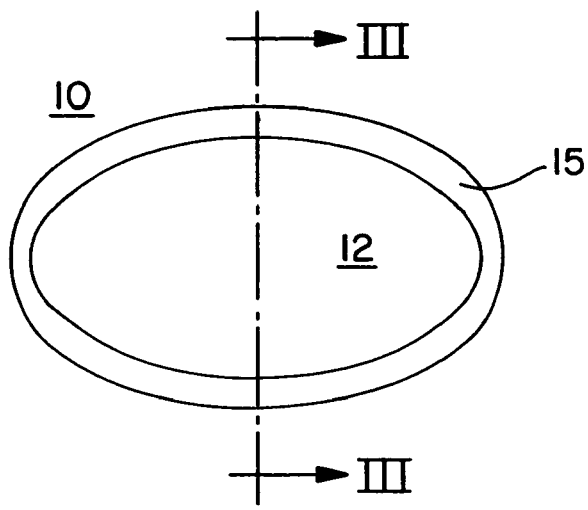
FIG. 2 shows another view depicted from the back or inner side of the embodiment of FIG. 1.

Turning now to FIG. 2, a critical view of backside 12 of artificial eye 10 is illustrated. As shown, backside 12 is generally concave in shape, although it should be noted that the shape may be altered as desired. For example, for manufacturing or other reasons a flat back may be preferred. The term "partially hemispheric" is applied to eyes in accordance with the present invention having either concave or flat backs. As another example, a projection, such as a screw, post, etc., may extend from the back in order to mount the eye. Nevertheless, in a preferred embodiment of the present invention, the edge 15 of the artificial eye is intended to mate with a complementary recess on the manikin, as will be further described below.

Figure 4:
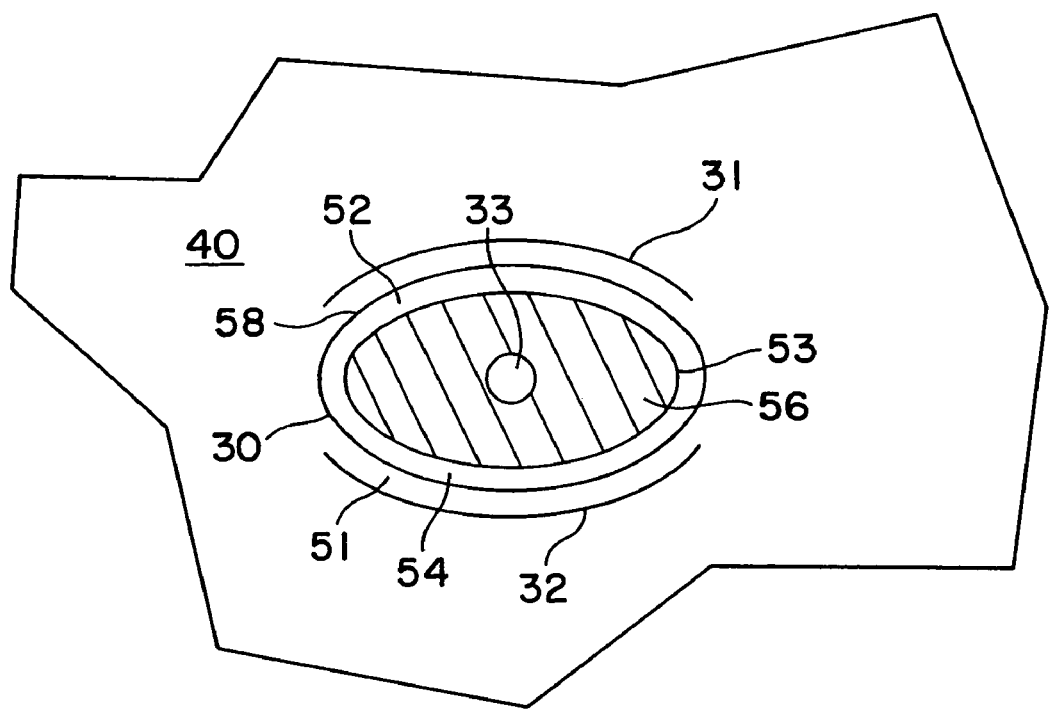
FIG. 4 shows a front view of a preferred eye socket embodiment on a manikin.

The concave eye shape of the preferred embodiment is perhaps best visualized as a wedge of cantaloupe or other hollow fruit. For example, if cut in half on a plane crossing the midpoint of a spherical melon (a hemisphere), the flesh would have two concentric surfaces—an outside convex side and a matching inner concave side following, in general, the same or similar curvature as the outer convex side. When this concept is transferred to the artificial eyes of the preferred embodiment, the outer convex side is the visible portion 11 of the eye when mounted, while the inner concave side is the back or inner side 12 of the mounted eye. Further in the preferred artificial eye embodiments of the present invention, the partially hemispherical front surface of the eye can be visualized as having two concentric surfaces—a front, visible, convex side 11, and a back, concave side 12 that is affixed to the manikin eye socket or mounting device, e.g., as illustrated in FIG. 4. This is referred to herein as a "modified" artificial eye configuration or a "modified, partially hemispherical" artificial eye configuration.

Figure 3:
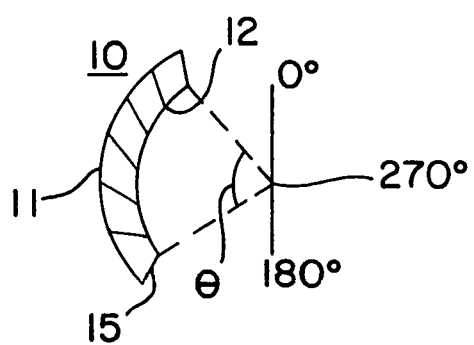
FIG. 3 shows a sectional view of the embodiment of FIG. 1.

Referring to FIG. 3, which is a side view taken along lines III-III of a preferred artificial eye embodiment as shown in FIG. 2, the eye has a generally arc like appearance or wedge, having an included angle θ of less than 180° (as shown by the dashed line projections of the angle in FIG. 3). Thus, a "modified" partial hemispherical preferred embodiment, rather than a hemisphere is shown. The angle of the arc and the amount of the outer hemisphere showing in the mounted eye vary depending upon the application, species being depicted, and/or personal preference as described above.

The backside of the preferred modified, partially hemispherical artificial eye configuration is generally concave, but the shape may be altered as necessary or desired. For example, although a concave shape is preferred, for manufacturing or other reasons a flat back may be more acceptable. In certain embodiments, a projection, such as a screw or a mounting post may extend from the back of the eye-piece for mounting purposes, but the entire eye-piece in such embodiments are still generally referred to herein as the eye.

When the modified, partially hemispherical artificial eye configuration is used, the eye-mounting area 49 of the manikin may be molded into a convex arc that matches the concave form of the backside 12 of eye 10. However, turning to FIG. 4, a view is presented of eye mounting area 40, comprising eye socket 30, such as might be seen on a manikin or the like in accordance with a preferred embodiment of the present invention. Eye socket 30 is molded into and forms an integral part of the manikin, and comprises a recess 56 (which may be called an "eye slot"), having an upper rim 58 and a lower rim 51. Upper rim 58 has an upper surface 52; whereas lower rim 51 has a lower surface 54. Upper surface 52 and lower surface 54 preferably meet and surround eye socket 30, although embodiments may exist in which the upper and lower surfaces of the eye socket do not completely surround the eye socket. Upper and lower surfaces 52 and 54 are oriented and have an area, such that eye socket 30 provides correct orientation of eye 10 when it is set in place in eye socket 30.

Preferably surface 53 mates with a corresponding surface on artificial eye 10, e.g., with inner eye edge surface 15 (as shown in FIG. 2). In the alternative, however, other embodiments may use methods of fastening so that a flattened edge surface, such as 15, is not necessarily present. In another alternative embodiment, even if present, surface 15 is not always used for fastening, as in the case of a friction fit, wherein the eye is held in place by the animal skin as described below.

As further shown in FIG. 4, eye slot 56 is defined by its outer edge 30. In a preferred embodiment of the present invention, outer edge 30 of eye socket substantially corresponds with the shape of a natural eye recess. For example, a deer manikin embodiment would preferably have two recesses (one for each eye) located in the appropriate natural positions on the head, and each recess corresponds to the shape of each of the deer's eyes. Recess 56 and outer edges 30 are positioned in preferred embodiments to reflect appropriately the same horizontal and vertical axis for the artificial eye placement as would exist in the naturally occurring animal.

The ridges forming upper and lower eyelids 31 and 32, respectively, are generally located above the upper and below the lower eye socket rims 51 and 58, respectively, at a distance and orientation relative to the eye corresponding to that which is seen in the animal in nature. Eyelids 31 and 32 are preferably an integral part of mounting surface 40, and are made of the same material as the molded manikin, or of a material that is compatible therewith. For example, the preferred material is an easily molded and sculpted material, such as polyurethane or lightweight urethane foam, or any material know or yet to be discovered for such purposed by those skilled in the relevant art. Such material is solid and firm, as opposed to modeling clay which remains soft and can be distorted for a length of time until dry, but the molded material retains the ability to be cut, drilled or carved, or to hold an inserted pin of the type used to hold the animal skin in place around the eye of the manikin.

The eyelids 31 and 32, respectively, in a preferred embodiment are molded into the manikin, and provide reference for placement of the skin. The molded eyelids can be removed, if desired, from the manikin, for example, by sanding or other abrasive means, without interfering with eye orientation. However, other embodiments may dispense with eyelids altogether, as desired. Alternatively, clay or other malleable materials may be used to model eyelids after the initial construction of the manikin.

Figure 5:
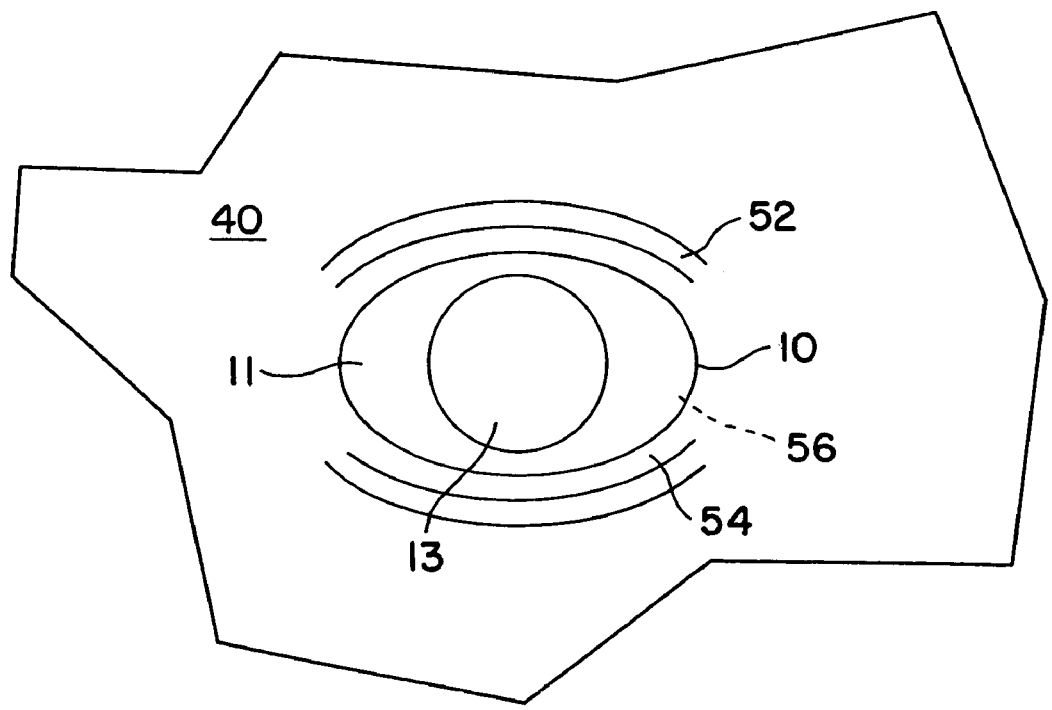
FIG. 5 shows a front view of the artificial eye embodiment of FIG. 1 in place in the eye socket embodiment of FIG. 4 on the manikin.

Preferred embodiments of the artificial eye of the present invention further comprise a pupil 13 embedded in the eye-piece material. An illustration of artificial eye 10, placed into recess 56, is shown in FIG. 5. As shown (FIG. 5), eye 10, in accordance with the preferred embodiment of the present invention, is placed in recess 56 of eye socket 30, such that no portion of the recess remains visible (as shown by the dotted lines identifying recess 56 in FIG. 5). The front surface 11 and pupil 13 of the artificial eye are visible, and pupil 13 is oriented into the desired position. The location of the pupil provides a correct orientation of the eye within the eye socket and shows which direction the eye would appear to be looking in the finished mount. The orientation of the pupil is key to the focus of the eye in a naturally occurring animal, and the proper location and orientation of the eyes serve similar critical roles in the realistic, life-like appearance of the finished mount. For example, in nature the eyes of most animals look forward at about 45° and slightly downward, so the mold is formed to place the pupil of the artificial eye such that the finished mount appears to be natural.

In addition the eyelids of the eye mounting area are molded in a "positive draft," meaning that upper and lower lids 31 and 32 are angled slightly in relation to the eye recess as would be understood by one familiar with the taxidermy arts.

Moreover, returning to FIG. 4, an indentation mark 33 is provided as a center point for the eye for various taxidermy tasks, such as in alternative embodiments of the present invention. For example, the center point 33 acts as a central reference to enlarge eye socket 30, e.g., by reducing upper and lower surfaces 52 and 54. In accordance with one alternative embodiment, a thin portion of surfaces 52 and 54 are cut or drilled out by the taxidermist, e.g., by using a spade bit centered on point 33 as a reference, to allow room for a conventional eye (e.g. a 180° hemispherical eye of the prior art) and eye socket 30. Thus, the eye may be fastened to eye socket 30 and held in place by the drape. Any tool may be utilized by the taxidermist using reference point 33. However, the positioning of the eye, even after drilling or cutting of the eye socket, for example to install a differently shaped eye onto the manikin, should remain as natural as possible and accurately represent the life-like positioning of the eye of the animal being sculptured.

Other modifications may also be made as would be recognized by one of ordinary skill in the taxidermy or sculpting arts. For example, skin may be mounted onto the manikin under the eye, or tucked behind the eye between the eye and the eye socket. To facilitate this skin tuck method, the taxidermist may cut lines above and below, or on either side of, or surrounding, recess 56 of eye socket 30. The cut lines, however, are actually just at the edge of the recess, just as taxidermists cut lines around the eye of conventional mounts. However, because the eye is removed from the recess during the cutting process in the present invention, the eye itself is not at risk of being scratched, damaged or shattered when touched by the cutting tool. In the preferred embodiment, after the skin of the cape is tucked into the cut lines, the eye is then installed, completely covering the tucked folds of skin. In the alternative, after the cuts are made, the partially hemispherical eye configuration is placed over the recess, after which the skin is then pressed into and fills all remaining space in the cut.

FIG. 5 also shows the mating of the eye (embodied in FIG. 1) with recess 56 of eye socket 30 (embodied in FIG.

4). The eye 10 and pupil 13 are set in a life-like orientation in the manikin by the mating of the front, convex, outer surface as shown between eyelids 31 and 32, such that edge 15 of eyepiece 10 is matched with surfaces 52 and 54 of eye socket 30. The skin or cape is then fitted over the manikin, and the skin is next tucked around the eye, or otherwise applied or adjusted as desired. In certain embodiments of the present invention, as noted above, the artificial eye may be installed after the placement of the cape over the manikin. In either case, optimally, when the present invention is used to place the eyes, no further manipulation is necessary to correctly position each eyepiece.

The upper and lower rims 51 and 58 of eye socket 56 and the upper and lower eyelids 31 and 32, respectively, are integral parts of the selected manikin. Moreover, front surface 11 of eyepiece 10 has a shape intended to tightly fit within the eye-surrounding features such that the exposed front portion of the eye is substantially the same as that of a living animal. Consequently, in accordance with the preferred embodiments of the invention, clay is not needed to fill any space around eyepiece 10. This is because either no space remains after eye 10 has been inserted into the cut lines, if any, or the draped skin fills all remaining space within the recess 56 when the skin is pressed into place around and under the concave backside of the modified partially hemispherical artificial eye configuration 10. Additional clay is not required for sculpting eye-surrounding features, since none need to be created because both recess 56 and eyelids 31 and 32 are part of the mold.

As a result, a taxidermist using a preferred embodiment of the present invention to position one or more artificial eyes 10 on the manikin having at least one, and almost always two matching eye socket(s) 30, comprising a recess 56 in the shape of the visible portion of a natural eye and surrounded by eye lids 31 and 32, requires far less time, knowledge of anatomy, or artistic ability to consistently achieve realistic results, as compared with known conventional techniques, because no additional sculpting is necessary. Matching the paired eyes is no longer a problem because the placement of each eye into the molded eye mounting socket of the preferred embodiment, automatically orients each eye into apparent focus with the other. Consequently, each completed taxidermy project using the present invention is routinely consistent and essentially indistinguishable from a comparable product of a highly skilled and experienced taxidermist using a conventional manikin, prior art eyepiece inserts and hand-sculpted eye-surrounding features. This is because there is no risk of movement of the artificial eye 10 once it has been fastened into eye socket 30.

Figure 6:
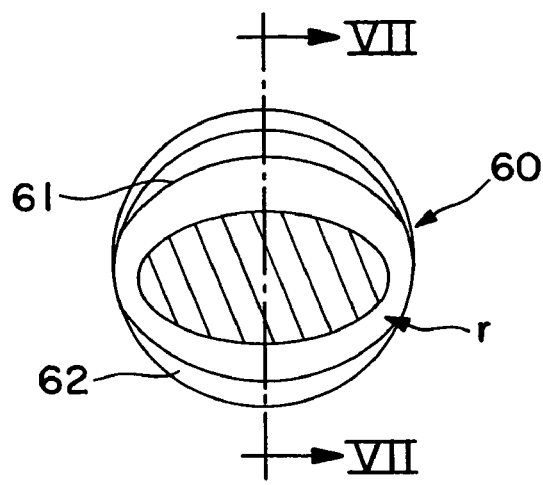
FIG. 6 shows a front view of an alternative preferred embodiment, intended for retrofitting a preferred eye embodiment into a conventional eye-mounting location in an existing manikin.

Embodiments also provide for retrofitting an eye embodiment of the present invention. FIG. 6 shows an eye-mounting piece 60, made of foam material, for retrofitting an eye embodiment (not shown). Eyelids 61 and 62 surround recess "r."

Figure 7:
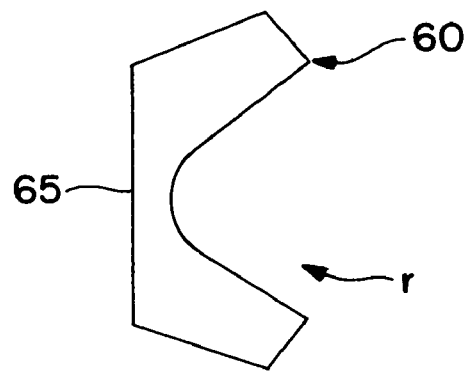
FIG. 7 shows a sectional view, taken along lines VII-VII, of the embodiment of FIG. 6.
Figure 8:
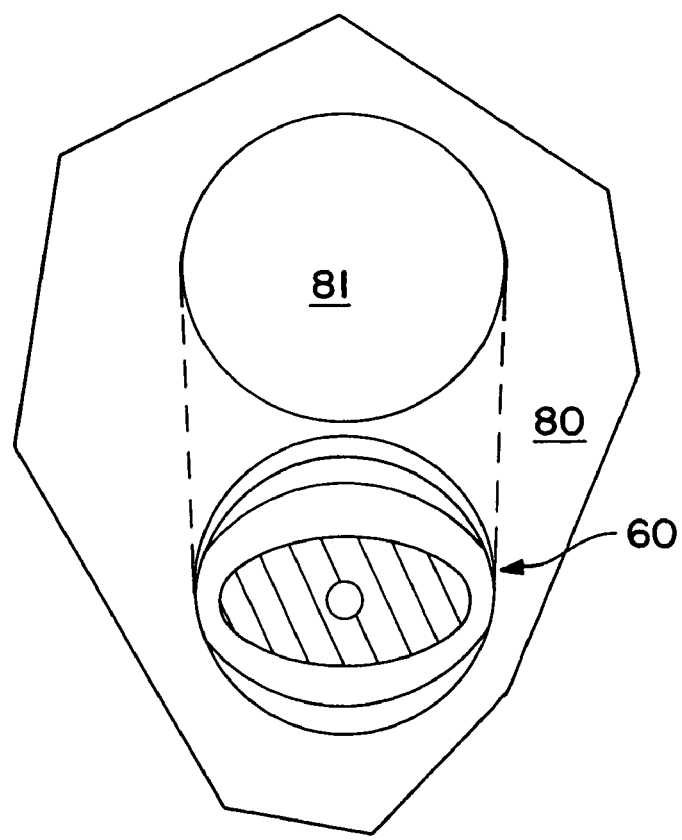
FIG. 8 shows another view of the embodiment of FIG. 6, wherein the embodiment of FIG. 6 is depicted as it would appear when placed into conventional recess 81 on retrofitted manikin 80.

FIG. 7 shows a cross sectional view of the embodiment depicted in FIG. 6, taken along lines VII-VII. As shown, backside 65 of eye mounting piece 60 is designed to fit within a conventional eye-mounting recess on a standard manikin. Then as shown in FIG. 8, when eye-mounting piece 60 is installed within recess 81 of conventional manikin 80, the recess conformationally operates as does recess 56 described above with regard to the preferred embodiments of FIGS. 1-5. As shown in the cut away view, the resulting recess after being filled with eye mounting piece 60 also appears and operates essentially as the eye mount of the preferred embodiment of FIGS. 1-5.

Eye mounting piece 60 is affixed with epoxy or other adhesive or bonding materials, of any type known in the art. The eye embodiment 60 is installed directly into recess 81, wherein the draped skin is drawn up to surround the eye and pressed in place as described above, leaving no residual space for movement of the inset eye. Alternatively, eye-mounting piece 60 may be configured so as to mate with a surface of eye 10, in a method similar to the mating described above with regard to the embodiments of FIGS 1-5. Fastening means, e.g., epoxy or adhesives, may then be used as desired.

A preferred method of mounting an artificial eye in a manikin in accordance with the present invention is further provided. In practice, a manikin is provided comprising at least eye socket 30 surrounded by upper and lower eyelids 31 and 32, respectively, and having a recess 56 that is generally in the shape of the visible portion of a natural eye for the particular species being modeled. A modified, partially hemispheric modified artificial eye 10 is provided that is also in the shape of the visible portion of a natural eye of the species. Artificial eye 10 is then positioned in eye socket 30, and then fastened to hold the eye 10 in place. Recess 56 and the concave back or inner side 12 of eye 10, when mated provide a cavity into which the draped skin covering the manikin can be tucked and tightly fastened around the eye to further prevent unwanted movement of the eye after it has been positioned, and to securely hold the skin in position in the eye-mounting area without distortion of the eye-surrounding features.

In the preferred embodiments of the invention, the artificial eyes are made of glass, although acrylic or other transparent materials known in the art to produce life-like eyes may be used. Additionally, the preferred manikin embodiments and eye mounting piece embodiments are "molded," i.e., constructed in mold to create the body shape, including the eye mounting area and eye-surrounding features characteristic of the animal being sculpted. The manikins, eye mounting area and eye-surrounding features are usually made of polyurethane foam or other moldable and easily carved or shaped material known in the art for producing conventional manikins. Other materials may be used as well so long as the necessary shapes can be molded, and providing that the appropriate recesses can be formed therein.

The entire manikin, including for the preferred embodiments of the present invention the eye mounting area and eye-surrounding features, may be molded and produced as a single piece. Alternatively the body of the manikin may be molded as a conventional piece, then the molded eye mounting area and eye-surrounding features as disclosed in the present invention may be subsequently added to the molded manikin body, to provide the area to which the artificial eye embodiments are then affixed.

Additionally, it should be noted that various embodiments may be used in a variety of types of sculptures, such as artistic sculptures, dolls, toys, etc., with appropriate materials, as are known in the art or which may be later discovered to be useful for artificial eye embodiments and body embodiments.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

I claim:

1. A sculpture for mounting at least one artificial eye, comprising at least one molded eye mounting area further comprising:
   (a) a molded eye socket having an upper rim having an upper surface, and a lower rim having a lower surface;
   (b) a molded upper eyelid positioned above and a lower eyelid positioned below the upper and lower rims, respectively; and
   (c) a molded recess formed between the upper and lower surfaces of the upper and lower rims;
   (d) wherein the upper and lower surfaces are molded such that placement of the at least one eye in the eye socket correctly orients the eye on the sculpture.

2. The sculpture of claim 1, wherein an eye mounted thereon is configured in a partially hemispherical configuration.

3. The sculpture of claim 2, wherein the mounting area is on a sculpture selected from the group consisting of taxidermy manikins, dolls, toys, stuffed toy animals, clothing mannequins, and artistic sculptures.

4. The sculpture of claim 3, wherein the mounting area is on a taxidermy manikin.

5. A sculpture having at least one artificial eye, comprising:
   (a) an artificial eye of partially hemispherical configuration, comprising a front convex side and a back side, wherein the back side is configured so as to be installed within a molded eye mounting area of the sculpture, and
   (b) a sculpture having a molded eye mounting area, comprising a molded eye socket having an upper rim having an upper surface, and a lower rim having a lower surface; a molded upper eyelid positioned above and a lower eyelid positioned below the upper and lower rims, respectively; and a molded recess formed between the upper and lower surfaces of the upper and lower rims;
   (c) wherein the upper and lower surfaces are molded such that placement of the at least one eye in the eye socket correctly orients the eye on the sculpture.

6. The sculpture of claim 5, wherein the artificial eye further comprises an edge around the outer circumference of the backside, and wherein the upper and lower surfaces of the upper and lower rims of the eye mounting area are molded such that placement of the eye in the eye socket also mates the edge of the eye to the upper and lower surfaces of the mounting area and correctly orients the eye on the sculpture.

7. The artificial eye of claim 6, wherein the sculpture having at least one artificial eye is selected from the group consisting of taxidermy manikins, dolls, toys, stuffed toy animals, clothing mannequins, and artistic sculptures.

8. The artificial eye of claim 7, wherein the eye is affixed to the mounting area on a taxidermy manikin.

9. The artificial eye of claim 5 wherein the eye comprises a modified partially hemispherical artificial eye configuration and the back side of the eye is concave.

10. The artificial eye of claim 5, wherein the convex front surface of the eye is aspheric in shape.

11. The artificial eye of claim 5, wherein the eye is manufactured from glass or acrylic material.

12. The artificial eye of claim 11, wherein the eye is manufactured from glass.

13. A method for mounting at least one partially hemispherical artificial eye in a sculpture, comprising the steps of:
   (a) providing an artificial eye comprising a partially hemispherical configuration having a front convex side and a back side;
   (b) providing at least one molded eye mounting area on the sculpture, said eye mounting area comprising a molded eye socket having an upper rim having an upper surface, and a lower rim having a lower surface; a molded upper eyelid positioned above and a lower eyelid positioned below the upper and lower rims, respectively; and a molded recess formed between the upper and lower surfaces of the upper and lower rims; wherein the upper and lower surfaces are molded such that placement of the at least one eye in the eye socket correctly orients the eye on the sculpture;
   (c) installing the at least one artificial eye in the at least one molded eye socket.

14. The method of claim 13, further comprising:
   (a) configuring an edge around the outer circumference of the backside of the artificial eye, and
   (b) molding the upper and lower surfaces of the upper and lower rims of the eye mounting area such that installing the eye in the eye socket also mates the edge of the eye to the upper and lower surfaces of the mounting area, correctly orienting the eye on the sculpture.

15. The method of claim 13, wherein the sculpture is selected from the group consisting of taxidermy manikins, dolls, toys, stuffed toy animals, clothing mannequins, and artistic sculptures.

16. The method of claim 15, wherein the sculpture is a taxidermy manikin.

17. The method of claim 13, wherein the artificial eye comprises a modified partially hemispherical artificial eye configuration and the back side of the eye is concave.

* * * * *